Figure 1:
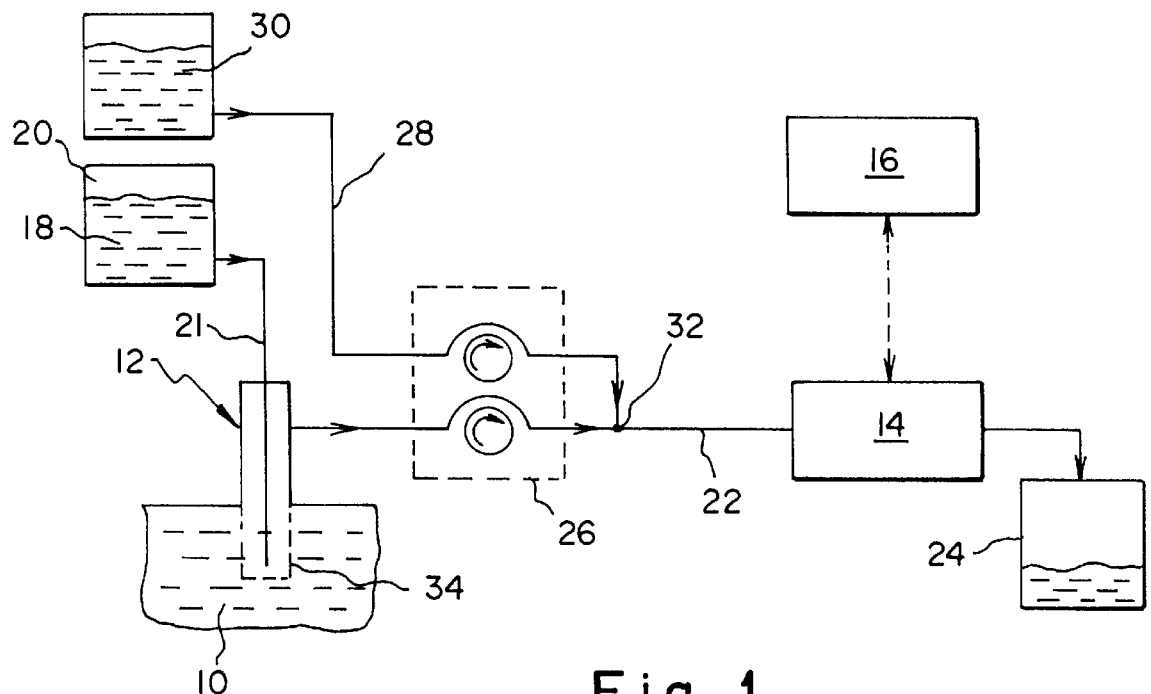

United States Patent
Pfeiffer et al.

[11] Patent Number: 6,091,976
[45] Date of Patent: Jul. 18, 2000

[54] DETERMINATION OF GLUCOSE CONCENTRATION IN TISSUE

[75] Inventors: Margret Pfeiffer; Udo Hoss, both of Ulm, Germany

[73] Assignee: Roche Diagnostics GmbH, Mannheim, Germany

[21] Appl. No.: 09/147,207

[22] PCT Filed: Mar. 4, 1997

[86] PCT No.: PCT/EP97/01075
  § 371 Date: Oct. 28, 1998
  § 102(e) Date: Oct. 28, 1998

[87] PCT Pub. No.: WO97/42868
  PCT Pub. Date: Nov. 20, 1997

[30] Foreign Application Priority Data

May 9, 1996 [DE] Germany .......................... 196 18 597

[51] Int. Cl.[7] .............................. A61B 5/05; A61B 5/00
[52] U.S. Cl. .......................... 600/347; 600/345; 600/365; 600/366
[58] Field of Search .................... 600/347, 345, 600/378, 352, 354, 365, 366, 368

[56] References Cited

U.S. PATENT DOCUMENTS

| | | | |
|---|---|---|---|
| 3,902,970 | 9/1975 | Levin | 205/777.5 |
| 4,786,372 | 11/1988 | Jones et al. | 205/781.5 |
| 5,441,481 | 8/1995 | Mishra et al. | 604/29 |
| 5,607,390 | 3/1997 | Patsalos et al. | 604/29 |
| 5,615,671 | 4/1997 | Schoonen et al. | 600/368 |
| 5,640,954 | 6/1997 | Pfeiffer et al. | 600/345 |
| 5,672,319 | 9/1997 | Eisum | 422/82.02 |

FOREIGN PATENT DOCUMENTS

| | | |
|---|---|---|
| 0 256 415 | 2/1988 | European Pat. Off. . |
| 41 30 742 A1 | 3/1993 | Germany . |
| 44 26 694 | 2/1996 | Germany . |

OTHER PUBLICATIONS

International Publication No. WO 94/06019 published Mar. 17, 1994.

*Primary Examiner*—Cary O'Connor
*Assistant Examiner*—Navin Natnithithadha
*Attorney, Agent, or Firm*—Arent Fox Kintner & Kahn, PLLC

[57] ABSTRACT

A method for determining and monitoring tissue glucose concentration, wherein a perfusion solution is conveyed as a liquid column through a microdialysis probe implanted in the tissue and is moved to a test cell preferably arranged outside the patient's body, the volumetric flow of the perfusion solution being reduced in its time average for the duration of the dialysis intervals $(T_1)$ and the volume of the perfusion solution perfused through the microdialysis probe during each dialysis interval $(T_1)$ being moved on in a consecutive transport interval $(T_2)$ at a higher volumetric flow to the test cell and wherein the glucose content of the perfusion solution passing through the test cell is determined from continuously detected test signals, characterized in that before passing through the microdialysis probe the perfusion solution is mixed with glucose in order to set a predetermined initial concentration.

14 Claims, 1 Drawing Sheet

DETERMINATION OF GLUCOSE CONCENTRATION IN TISSUE

DESCRIPTION

The invention relates to a method and apparatus to determine and monitor the concentration of tissue glucose as defined in the preambles of the independent claims 1 and 17.

Methods of this kind are applicable foremost in human medicine, in particular to monitor the blood sugar of diabetics. They are based on the insight that the glucose content of the interstitial tissue fluid is highly correlated, with little time delay, to the blood sugar level. It is known to recover glucose by dialysis and then to determine the glucose content by enzymatic-amperometric measurements in an flow-through test cell. For that purpose a continuous flow of perfusate is made to pass along the dialysis membrane of the dialysis probe. The yield so obtained depends essentially on the rate of perfusion and as a rule is less than 30%. The measurement is commensurately inaccurate because interfering factors such as tissue movement and changes in blood circulation strongly affect the yield and hence the test signal. Lowering the perfusion rate will not help because entailing a correspondingly higher dead time caused by the flow time between the microdialysis probe and the test site. On the other hand, high rates of flow velocity do indeed lower the dead time. However the dialysis yield relative to a unit volume of perfusion solution decreases to the same extent. Moreover a glucose gradient is formed in the tissue surrounding the microdialysis probe on account of continuously withdrawing glucose. However long-term treatment of diabetics mandates reliable glucose measurements to dose insulin administrations as needed and, where desirable, automatically.

Based on the above, the objective of the invention is to create a method and apparatus of the initially cited kinds which offer high reliability and accuracy as regards glucose determination.

The combinations of features stated in the patent claims 1 and 17 are proposed as solutions. Further advantageous implementations of the invention are stated in the dependent claims.

The conventional continuous enrichment of the perfusion solution is replaced in the invention by equalizing the liquid column, moved in segments with high yield through the microdialysis probe, and the tissue glucose content. Accordingly the invention proposes to reduce the time-averaged volumetric flow of the perfusion solution for the duration of dialysis intervals and that the volume of perfusion solution perfused during each dialysis interval through the microdialysis probe shall be moved on in an ensuing transport interval at a higher volumetric flow to the test cell. The equalization of concentration taking place during the dialysis intervals averts continuous impoverishment of the tissue. At the same time, high signal strength is achieved because of the higher yield. The enriched partial volumes can be moved at a higher conveyance flow and thus with a lesser dead time to the test cell.

In a preferred implementation of the invention, the perfusion solution is mixed with glucose before being made to pass through the microdialysis probe and a predetermined initial concentration is set, preferably within the physiological range. Using an initial solution mixed with glucose leads to diffusion enrichment or impoverishment at the dialysis membrane depending on the tissue glucose concentration. Accordingly a signal peak or a signal dip is observed in the time-sequence of the test signals at the test cell. On the other hand the subsequent perfusion solution passing at a higher flow during the transport intervals through the microdialysis probe essentially retains its initial glucose concentration. Accordingly a base line reflecting the initial glucose concentration is picked up during the subsequent flow through the cell.

Advantageously the volumetric flow of perfusion solution is so adjusted during the transport intervals that the glucose content of the perfusion solution changes less than 10%, preferably less than 5%, on account of the reduced duration of dialysis, when passing through the microdialysis probe. On the other hand, in order to increase the accuracy of measurement, the volumetric flow during the dialysis intervals should be adjusted in such manner that the glucose content of the perfusion solution essentially matches the concentration of tissue glucose when passing through the microdialysis probe.

Advantageously a base line value is determined from the test signals picked up at the test cell during the flow-through of the volume of the perfusion solution perfused at higher-volumetric flow, said base line value reflecting the initial glucose concentration and thereby allowing continuous signal correction for instance in the event of fluctuations in test sensitivity.

Advantageously the peak test signals ascertained during the transport intervals at the test cell when crossed by the enriched liquid-column segments are evaluated with respect to their extreme value, hereafter called extremum/extrema, or of their integrated value, to determine the tissue glucose concentration.

Advantageously the tissue glucose concentration is determined in each transport interval from the ratio of the extremum to the base line value of the test signal multiplied by the value of initial glucose concentration and where called for by a predetermined calibration value. This procedure allows constantly updated calibration of the glucose test values and compensating any signal drifts. In this manner spurious measurements can be precluded that otherwise might arise from conveyance malfunctions or interferences in the test cell.

Because of the peak-shaped signal sequence of the test signals, validity testing is feasible in that the predetermined time between the extrema of the test signals will be monitored by the time between the transport intervals.

Advantageously again, the signal sequence of the test signals is used for validity-checking the ascertained glucose content, a peak being expected as a valid signal shape when comparing a concentration value higher than the initially set glucose concentration and a dip for a lesser value of concentration. In this manner reliable, qualitative checking of the measurements is possible. Another increase in reliability of measurement can be achieved in that the initial glucose concentration is set to a sugar deficiency value and in that when the test signals undergo a dip in their sequence, a sugar-deficiency alarm is triggered. Moreover it is basically feasible to adjust the initial glucose concentration in phases alternatingly—for instance using a valve circuit—to a sugar deficiency value and an excess sugar value, an alarm signal being emitted at a dip during the phase of adjusted sugar deficiency value and at a peak during the phase of adjusted excess sugar value.

Qualitative pattern recognition in the sequence of the test signals is implemented in simple manner in that the extrema ascertained in the time between the transport intervals are compared with the particular associated base line value, where a peak shall be recognized when comparing an extremum larger than the base line value and a dip shall be recognized when comparing an extremum smaller than the base line value.

In another preferred implementation of the invention, the perfusion solution is moved during the dialysis intervals always in several, time-separated conveyed batches through the microdialysis probe. Thereby the glucose-enriched segment of the liquid column is widened and correspondingly the diffusion decay will be reduced during the ensuing transport interval.

When seeking high yield in the dialysis, advantageously a volume of the perfusion solution substantially corresponding to the volume of the microdialysis probe is moved at each conveyed batch. Another improvement can be achieved in this respect by so sizing the conveyance pauses between conveyed batches that the glucose content of the perfusion-solution volume instantaneously present in the microdialysis probe shall substantially equal the tissue glucose concentration.

In an alternative to the batch-conveyance, the volumetric flow of the perfusion solution may be reduced to a constant value for the duration of the dialysis intervals.

The initially cited problem regarding the measurement apparatus is solved in that at least one glucose reservoir containing glucose in a predetermined initial concentration can be connected to the perfusate line. In order to ascertain whether the tissue glucose represents a deficiency or excess of sugar, two glucose reservoirs separately connectable to the perfusate line may be used, each containing dissolved glucose of a different concentration.

Advantageously the at least one glucose reservoir shall be connectable through a switching valve to the perfusate line to allow mixing the perfusion solution selectively at separate times and/or if called for at a different concentration to the perfusate line.

A defined batch-wise conveyance of the perfusion solution, which may be enriched with glucose, can be implemented by using a metering pump preferably operated at intervals as the conveyor unit.

The invention is elucidated below in relation to an illustrative embodiment which is schematically shown in the drawing.

Figure 2:
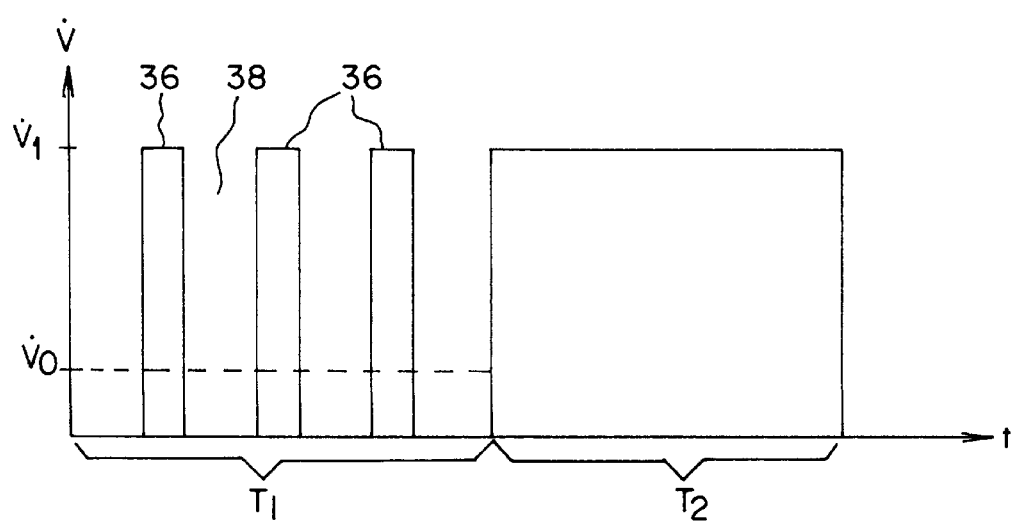

FIG. 1 shows a microdialysis system to measure subcutaneous glucose concentration, and FIG. 2 is a time plot of the volumetric flow of the perfusion solution through the system of FIG. 1.

The method of the invention to subcutaneously measure tissue glucose is based on the principle of microdialysis and can be carried out using the measuring apparatus shown in FIG. 1. Essentially this measuring apparatus consists of a microdialysis probe 12 implantable into the patient's subcutaneous fatty tissue 10, of an through-flow test cell 14 located outside the patient's body and a signal-processing unit 16 cooperating with the test cell 14. To withdraw a sample from the tissue 10, a perfusion solution 18 is pumped out of a reservoir 20 through a perfusate line 21 as a continuous column of liquid while passing through the microdialysis probe 12 and by means of a connecting line 22 through the test cell 14 into a collecting vessel 24. This pumping is implemented by a two-channel roller metering pump 26 inserted into the connecting line 22. The second channel of the roller metering pump 26 is loaded at its intake side through a line 28 with an enzyme solution 30 which is fed at its outlet side at a mixing station 32 into the connecting line 22.

When the perfusion solution 18 flows through the microdialysis probe 12, a glucose diffusion exchange takes place at the glucose-permeable dialysis membrane 34 between the perfusion liquid and the tissue liquid. Depending on the concentration gradient, the perfusion solution 18 flowing past the membrane 14 is enriched with tissue glucose. Thereupon the glucose content of the perfusion solution is determined in known manner, using an electrochemical/amperometric sensor, in the test cell 14, as an electrode signal and is analyzed in the signal processing unit 16. The basic detection reactions catalyzed by the enzyme solution 30 are described in detail in the German Offenlegungsschrift 44 01 400, and are explicitly referred to herewith. In an alternative, the glucose also may be detected using an enzyme sensor as described in the German Offenlegungsschrift 41 30 742.

The conveyance of the perfusion solution 18 through the pump 26 is carried out in the invention at predetermined time intervals in the manner shown in FIG. 2. The perfusion solution is moved during a dialysis interval $T_1$ at several mutually distinct and consecutive times in conveyed batches 36, each conveyed batch 36 corresponding substantially to the volumetric content of the microdialysis probe 12. The conveyance pauses 38 between the conveyed batches 36 are selected in such manner that the glucose content of the particular volume of perfusion solution 18 in the microdialysis probe 12 substantially equals the tissue glucose concentration. In principle the volumetric flow of the perfusion solution 18 also may be reduced to a constant value $dV_0/dt$ for the duration of the dialysis interval, whereby the transmitted quantity of perfusion solution 18 during the time interval $T_1$ corresponds to that of the batch conveyance. However the pump 26 then must be adjustable in its flow.

The volume of perfusion solution 18 enriched in the probe 12 during the interval $T_1$ is pumped during the course of the ensuing transport interval $T_2$ at a constant volumetric flow $dV_1/dt$ determined by the flow output of the pump 26 into the test cell 14. On account of the higher speed of flow, the trailing perfusion solution 18 flowing in this phase through the microdialysis probe 12 is hardly laden with glucose from the tissue 10. Therefore the test signal from the test cell presents a peak value when the enriched segments of the liquid column are moved past and it will show a base line value when liquid volumes passing through the probe 12 with short durations of perfusion are being transported. Accordingly the base lines and the extrema can be measured at predetermined times within the total time interval $T_1+T_2$. Typical conveyance flows are 0.3–1 μltr/min for $T_1$ and 5–50 μltr/min for $T_2$.

Improved analysis, in particular regarding signal drift and validity, is implemented in that the perfusion solution 18 in the reservoir 20 is mixed with glucose. The initial concentration within the physiological range is set for instance at 5 mmole/ltr. Alternatively however, the glucose solution can be prepared separately from the perfusion solution 20 in separate glucose reservoirs appropriately and selectively communicating through switching valves with the perfusate line 21.

If the test sensor is linear, tissue glucose can be ascertained by the fact that the ratio of the extremum detected during the interval to the associated base line value is multiplied by the value of the initial glucose concentration and where called for by a calibration factor. The calibration factor can be determined by a one-time in-vivo comparison measurement of the glucose levels in the blood and in the tissue. Appropriately an offset ascertained by a one-time in-vitro measurement before implantation while dipping the probe 12 into a glucose-free test solution shall be taken into account. Adding glucose to the perfusion solution 18 therefore allows automatically recalibrating the test signals once an initial calibration was carried out.

Signal validity can be monitored merely by pattern recognition. A peak is obtained when comparing a glucose content of the tissue 10 which is higher than the adjusted concentration, and a dip if the glucose content is lower. Illustratively a signal shape which deviates because of zero shift can be detected in this manner as being invalid. In this manner it is possible also to monitor a patient's glucose level within a predetermined range by means of simple qualitative comparison measurements. For instance the initial glucose concentration in the perfusion solution 30 may be alternatingly adjusted to a sugar-deficiency value and to an excess sugar value, a warning signal being emitted for a dip in the sequence of the test signals during the phase adjusted sugar-deficiency concentration and for a peak during the phase of adjusted sugar-surplus concentration.

In this procedure, signal shape recognition is restricted to detecting two measurement values in each case, namely an extremum associated with the high glucose yield during the dialysis interval $T_1$ and a base line value associated with the low glucose yield (because of the high volumetric flow $dV_1/dt$) during the transport intervals $T_2$. The two measurement values can be ascertained each at predetermined times within the time interval $T_1+T_2$, a peak being as the signal shape when comparing an extremum larger than the base line value, and a dip being assumed when comparing an extremum smaller than the base line value.

In summary, the invention relates to a method and apparatus for determining tissue glucose, a perfusion solution being moved as a liquid column to pass through a microdialysis probe implanted in the tissue to a test cell. In order to increase yield, to avert concentration gradients and to reduce the dead time, the invention proposes that the volumetric flow V of the perfusion solution over the duration of the dialysis intervals $T_1$ be reduced to a time-averaged value of $dV_0/dt$ and that the volume of the perfusion solution which is perfused through the microdialysis probe during each dialysis interval $T_1$ be moved in each ensuing transport interval $T_2$ at a higher volumetric flow $dV_1/dt$ to the test cell.

What is claimed is:

1. Method for determining and monitoring tissue glucose concentration, wherein a perfusion solution (18) is conveyed as a liquid column through a microdialysis probe (12) implanted in the tissue (10) and is moved to a test cell (14) preferably arranged outside the patient's body, the volumetric flow of the perfusion solution (18) being reduced in its time average for the duration of the dialysis intervals ($T_1$) and the volume of the perfusion solution (18) perfused through the microdialysis probe (12) during each dialysis interval ($T_1$) being moved on in a consecutive transport interval ($T_2$) at a higher volumetric flow to the test cell (14) and wherein the glucose content of the perfusion solution (18) passing through the test cell (14) is determined from continuously detected test signals, wherein before passing through the microdialysis probe (12) the perfusion solution (18) is mixed with glucose in order to set a predetermined initial concentration.

2. Method as claimed in claim 1, wherein the initial glucose concentration is set to be within the physiological range.

3. Method as claimed in claim 1, wherein the volumetric flow ($dV_1/dt$) of the perfusion solution (18) is adjusted in such manner during the transport intervals ($T_2$) that the glucose content of the perfusion solution (18) changes less than 10%, preferably less than 5% when the solution passes through the microdialysis probe (12).

4. Method as claimed in claim 1, wherein the volumetric flow ($dV_0/dt$) of the perfusion solution is adjusted in such manner during the dialysis intervals ($T_1$) that the glucose content of the perfusion solution (18) as it passes through the microdialysis probe (12) substantially equals the tissue glucose concentration.

5. Method as claimed in claim 1, wherein a base line value is determined from test signals picked up at the test cell (14) during the flow-through of the volume of the perfusion solution (18) perfused at the higher volumetric flow ($dV_1/dt$).

6. Method as claimed in claim 1, wherein the concentration of the tissue glucose is determined from the extremum or from the integral value of the test signals detected at the test cell (14) during each transport interval ($T_2$).

7. Method as claimed in claim 5, wherein the ratio of extremum to base line value of the peak- or dip-shaped signal sequence of the test signals is formed and is multiplied by the value of the initial glucose concentration and if necessary by a predetermined calibration factor to determine the tissue glucose concentration.

8. Method as claimed in claim 6, wherein the time separation of the extrema of the measurement values predetermined by the time interval ($T_1+T_2$) of the transport intervals $T_2$ is monitored to check the validity of the test signals.

9. Method as claimed in claim 2, wherein the signal sequence of the test signals detected during each transport interval ($T_2$) at the test cell (14) is analyzed to check the validity of the determined glucose content, a peak being expected as a valid signal shape when the concentration value is higher than the adjusted initial glucose concentration and a dip being expected for a lesser concentration.

10. Method as claimed in claim 2, wherein the initial glucose concentration is set at a sugar-deficiency value and that upon a dip in the sequence of the test signals a sugar-deficiency alarm is emitted.

11. Method as claimed in claim 2, wherein the initial glucose concentration is set in alternating phases to a sugar-deficiency value and to a sugar-excess value and that, upon a dip in the sequence of the test signals during the phase set to sugar-deficiency concentration, and upon a peak of the phase set to excess-sugar concentration, an alarm signal is emitted.

12. Method as claimed in claim 1, wherein the extrema determined in the time interval ($T_1+T_2$) of the transport intervals ($T_2$) are compared with the particular associated base line value to achieve qualitative pattern recognition of the sequence of the test signals, a peak being recognized as a signal shape when the extremum compared the the base line value is larger and a dip when the extremum is smaller.

13. Method as claimed in claim 1, wherein during each dialysis interval ($T_1$) the perfusion solution (18) is moved in several batches (36) mutually apart by a time interval (38) through the microdialysis probe (12).

14. Method as claimed in claim 13, wherein at each batch (36) a volume of the perfusion solution (18) essentially corresponding to the content of the microdialysis probe (12) is moved on.

* * * * *